US005587105A

United States Patent [19]

Sheppard et al.

[11] Patent Number: 5,587,105

[45] Date of Patent: Dec. 24, 1996

[54] METHODS FOR MAKING LIQUID MOLDING COMPOUNDS USING DIAMINES AND DICYANATES

[76] Inventors: Clyde H. Sheppard, Boeing Aerospace Company, P.O. Box 399, M/S 73-09, Seattle, Wash. 98124-2499; Hyman R. Lubowitz, 26 Coral Tree Ln., Rolling Hills Estates, Calif. 90274

[21] Appl. No.: 493,434

[22] Filed: Jun. 5, 1995

Related U.S. Application Data

[62] Division of Ser. No. 168,289, Mar. 15, 1988.

[51] Int. Cl.$^{6}$ ...................... C07D 209/02; C07D 209/56; C09K 3/00

[52] U.S. Cl. ................................ 252/183.11; 252/182.18; 252/182.26; 528/60; 528/64; 548/431; 548/435; 548/451; 548/455

[58] Field of Search ................................. 528/60, 64, 74, 528/83, 335, 329.1, 61, 73; 548/431, 435, 512, 451, 455; 252/182.18, 182.26, 183.11

[56] References Cited

U.S. PATENT DOCUMENTS

| | | | |
|---|---|---|---|
| H183 | 1/1987 | Karasz et al. . | |
| Re. 29,316 | 7/1977 | Bargain et al. . | |
| Re. 30,922 | 5/1982 | Heilman et al. . | |
| 3,105,839 | 10/1963 | Renner . | |
| 3,148,173 | 9/1964 | Axelrood | 528/60 X |
| 3,236,705 | 2/1966 | Gilman et al. . | |
| 3,236,808 | 2/1966 | Goldberg et al. . | |
| 3,262,914 | 7/1966 | Goldberg et al. . | |
| 3,265,708 | 8/1966 | Stiteler . | |
| 3,267,081 | 8/1966 | Rudner et al. . | |
| 3,313,783 | 4/1967 | Iwakura et al. . | |
| 3,354,129 | 11/1967 | Edmonds et al. . | |
| 3,355,272 | 11/1967 | D'Alessandro . | |
| 3,386,969 | 6/1968 | Levine . | |
| 3,408,349 | 10/1968 | Matsunaga . | |
| 3,431,235 | 3/1969 | Lubowitz . | |
| 3,435,003 | 3/1969 | Craven . | |
| 3,449,442 | 6/1969 | Williams et al. . | |
| 3,450,711 | 6/1969 | Megna et al. . | |
| 3,453,236 | 7/1969 | Culbertson . | |
| 3,454,673 | 7/1969 | Schmidt . | |
| 3,458,486 | 7/1969 | Ray et al. . | |
| 3,461,461 | 8/1969 | Anthony et al. . | |
| 3,525,717 | 8/1970 | Butler et al. | 528/83 X |
| 3,528,950 | 9/1970 | Lubowitz . | |
| 3,530,087 | 9/1970 | Hayes et al. . | |
| 3,536,670 | 10/1970 | Aeiony et al. . | |
| 3,562,223 | 2/1971 | Bargain et al. . | |
| 3,563,951 | 2/1971 | Dormagen et al. . | |
| 3,565,549 | 2/1971 | Lubowitz et al. . | |
| 3,592,841 | 7/1971 | Broadhead . | |
| 3,598,768 | 8/1971 | Bach . | |
| 3,598,786 | 8/1971 | Yoda et al. | 528/329.1 X |
| 3,609,181 | 9/1971 | Lubowitz et al. . | |
| 3,616,193 | 10/1971 | Lubowitz et al. . | |
| 3,624,042 | 11/1971 | Lubowitz et al. . | |
| 3,631,222 | 12/1971 | Vogel . | |
| 3,632,428 | 1/1972 | Lubowitz et al. . | |
| 3,635,428 | 1/1972 | Lubowitz et al. . | |

(List continued on next page.)

FOREIGN PATENT DOCUMENTS

| | | |
|---|---|---|
| 1175998 | 9/1984 | Canada . |
| 1269576 | 5/1990 | Canada . |
| 0152372 | 1/1985 | European Pat. Off. . |
| 0175484 | 3/1986 | European Pat. Off. . |
| 0067976 | 3/1987 | European Pat. Off. . |
| 0289695 | 1/1988 | European Pat. Off. . |
| 0283636 | 1/1988 | European Pat. Off. . |
| 0277476 | 8/1988 | European Pat. Off. . |
| 0292434 | 11/1988 | European Pat. Off. . |
| 0289798 | 11/1988 | European Pat. Off. . |
| 0292677 | 11/1988 | European Pat. Off. . |
| 0266662 | 11/1988 | European Pat. Off. . |
| 0294555 | 12/1988 | European Pat. Off. . |
| 0132547 | 2/1989 | European Pat. Off. . |
| 0305882 | 3/1989 | European Pat. Off. . |

(List continued on next page.)

OTHER PUBLICATIONS

St. Clair, et al., Additives Lower Pickup of Moisture by Polyimides, NASA Tech Briefs, 80–81 Apr., 1989.

Heidemann, "Oligomers", Encyclopedia of Polymer Science and Technology vol. 9 Molding to Petroleum Resins 485–506 1968.

Second–generation polymide raises continuous–use temperatures, Advanced Composites May/Jun., 1988.

Vanucci et al., 700°F Properties of Autoclave Cured PMR–II Composites, NASA Tech. Memo 100923 Sep., 1988.

Vanucci, PMR Polyimide Compositions for Improved Perfomance at 371°C, NTIS n87–16071 Apr., 1987.

Elsenbaumer et al., Highly Conductive Meta Derivatives of Poly(phenylene Sulfide), J. Polymer Sci: Polymer Phys. Ed., vol. 20, 1781–1787 1982.

Patel et al., Poly–Schiff Bases, I. Preparation of Poly–Schiff Bases from 4,4'–Diacetyl Diphenyl Ether (DDE) with Various Diamines, J. of Polymer Chem. Ed., vol. 20, 1985–1992 1982.

(List continued on next page.)

*Primary Examiner*—Richard D. Lovering
*Attorney, Agent, or Firm*—John C. Hammar

[57] ABSTRACT

Low molecular weight resins that usually are aliphatic and that include crosslinking thermal functional groups are useful as liquid molding compounds for reaction injection molding or resin transfer molding. The compounds eliminate the need to handle solvents when preparing thermoset composites.

10 Claims, No Drawings

U.S. PATENT DOCUMENTS

| | | | |
|---|---|---|---|
| 3,641,207 | 2/1972 | Lauchlan . | |
| 3,647,529 | 3/1972 | Lubowitz et al. . | |
| 3,652,710 | 3/1972 | Holub . | |
| 3,658,764 | 4/1972 | Bargain et al. . | |
| 3,658,938 | 4/1972 | Kwiatkowski et al. . | |
| 3,663,507 | 5/1972 | Vogel . | |
| 3,689,464 | 9/1972 | Holub et al. . | |
| 3,697,308 | 10/1972 | Lubowitz et al. . | |
| 3,697,345 | 10/1972 | Lubowitz et al. . | |
| 3,699,074 | 10/1972 | Lubowitz et al. . | |
| 3,699,075 | 10/1972 | Lubowitz . | |
| 3,708,370 | 1/1973 | Lubowitz et al. . | |
| 3,708,439 | 1/1973 | Sayigh et al. . | |
| 3,708,459 | 1/1973 | Lubowitz . | |
| 3,729,446 | 4/1973 | Holub et al. . | |
| 3,745,149 | 7/1973 | Serafini et al. . | |
| 3,748,311 | 7/1973 | Burns et al. | 528/335 X |
| 3,748,312 | 7/1973 | Burns et al. . | |
| 3,749,735 | 7/1973 | Loria . | |
| 3,757,088 | 9/1973 | Osborn . | |
| 3,759,777 | 9/1973 | Lubowitz et al. . | |
| 3,761,441 | 9/1973 | D'Alessandro et al. . | |
| 3,763,101 | 10/1973 | Jones et al. . | |
| 3,770,697 | 11/1973 | Holub et al. . | |
| 3,772,250 | 11/1973 | Economy et al. . | |
| 3,773,718 | 11/1973 | Klebe et al. . | |
| 3,781,240 | 12/1973 | Lubowitz et al. . | |
| 3,781,249 | 12/1973 | Lubowitz . | |
| 3,784,311 | 7/1973 | Burns et al. . | |
| 3,803,081 | 4/1974 | Lubowitz . | |
| 3,812,159 | 5/1974 | Lubowitz . | |
| 3,827,927 | 8/1974 | Lubowitz et al. . | |
| 3,839,287 | 10/1974 | Kwiatkowski et al. . | |
| 3,843,593 | 10/1974 | Shell et al. . | |
| 3,847,867 | 11/1974 | Heath et al. . | |
| 3,847,869 | 11/1974 | Williams, III . | |
| 3,853,815 | 12/1974 | Lubowitz . | |
| 3,859,252 | 1/1975 | Cho . | |
| 3,879,349 | 4/1975 | Bilow et al. . | |
| 3,879,393 | 4/1975 | Havera . | |
| 3,879,428 | 4/1975 | Heath et al. . | |
| 3,887,582 | 6/1975 | Holub et al. . | |
| 3,890,272 | 6/1975 | D'Alelio . | |
| 3,895,064 | 7/1975 | Brode et al. . | |
| 3,896,147 | 7/1975 | Stephen . | |
| 3,897,395 | 7/1975 | D'Alelio . | |
| 3,909,507 | 9/1975 | Betts et al. . | |
| 3,914,334 | 10/1975 | Lubowitz et al. . | |
| 3,919,177 | 11/1975 | Campbell . | |
| 3,920,768 | 11/1975 | Kwiatkowski . | |
| 3,925,324 | 12/1975 | Gerard . | |
| 3,933,862 | 1/1976 | Williams, III . | |
| 3,935,167 | 1/1976 | Marvel et al. . | |
| 3,935,320 | 1/1976 | Chiu et al. . | |
| 3,941,746 | 3/1976 | Stephen . | |
| 3,956,320 | 5/1976 | Heath et al. . | |
| 3,957,732 | 5/1976 | Hirooka et al. . | |
| 3,957,862 | 5/1976 | Heath et al. . | |
| 3,966,678 | 6/1976 | Gruffaz et al. . | |
| 3,966,726 | 6/1976 | Toth et al. . | |
| 3,966,987 | 6/1976 | Suzuki et al. . | |
| 3,970,714 | 7/1976 | Bargain . | |
| 3,972,902 | 8/1976 | Heath et al. . | |
| 3,988,374 | 10/1976 | Brode et al. . | |
| 3,991,026 | 11/1976 | Matsuda et al. | 528/60 X |
| 3,993,630 | 11/1976 | Darmory et al. . | |
| 3,998,786 | 12/1976 | D'Alelio . | |
| 4,000,146 | 12/1976 | Gerber . | |
| 4,005,134 | 1/1977 | Markezich . | |
| 4,013,600 | 3/1977 | Cassat . | |
| 4,020,069 | 4/1977 | Johnson et al. . | |
| 4,026,871 | 5/1977 | D'Alelio . | |
| 4,038,261 | 7/1977 | Crouch et al. . | |
| 4,051,177 | 9/1977 | Braden et al. . | |
| 4,055,543 | 10/1977 | D'Alelio . | |
| 4,058,505 | 11/1977 | D'Alelio . | |
| 4,060,515 | 11/1977 | D'Alelio . | |
| 4,064,289 | 12/1977 | Yokoyama et al. . | |
| 4,075,171 | 2/1978 | D'Alelio . | |
| 4,097,456 | 6/1978 | Barie . | |
| 4,100,137 | 7/1978 | Lemieux et al. . | |
| 4,100,138 | 7/1978 | Bilow et al. . | |
| 4,101,488 | 7/1978 | Ishizuka et al. . | |
| 4,107,147 | 8/1978 | Williams, III et al. . | |
| 4,107,153 | 8/1978 | Akijama et al. . | |
| 4,107,174 | 8/1978 | Baumann et al. . | |
| 4,108,837 | 8/1978 | Johnson et al. . | |
| 4,108,926 | 8/1978 | Arnold et al. . | |
| 4,111,879 | 9/1978 | Mori et al. . | |
| 4,115,231 | 9/1978 | Darms et al. . | |
| 4,115,362 | 9/1978 | Inata et al. . | |
| 4,116,937 | 9/1978 | Jones et al. . | |
| 4,124,593 | 11/1978 | Gschwend et al. . | |
| 4,126,619 | 11/1978 | Darms et al. . | |
| 4,128,574 | 12/1978 | Markezich et al. . | |
| 4,132,715 | 1/1979 | Roth . | |
| 4,132,716 | 1/1979 | Kvita et al. . | |
| 4,134,895 | 1/1979 | Roth et al. . | |
| 4,142,870 | 3/1979 | Lovejoy . | |
| 4,158,731 | 6/1979 | Baumann et al. . | |
| 4,166,168 | 8/1979 | D'Alelio . | |
| 4,167,663 | 9/1979 | Granzow et al. . | |
| 4,168,366 | 9/1979 | D'Alelio . | |
| 4,172,836 | 10/1979 | Baumann et al. . | |
| 4,174,326 | 11/1979 | Baumann et al. . | |
| 4,175,175 | 11/1979 | Johnson et al. . | |
| 4,176,223 | 11/1979 | Irwin . | |
| 4,179,551 | 12/1979 | Jones et al. . | |
| 4,183,839 | 1/1980 | Gagliani . | |
| 4,187,364 | 2/1980 | Darms et al. . | |
| 4,189,560 | 2/1980 | Roth et al. . | |
| 4,193,927 | 3/1980 | Baumann et al. . | |
| 4,197,397 | 4/1980 | D'Alelio . | |
| 4,200,731 | 4/1980 | Massey et al. . | |
| 4,206,106 | 6/1980 | Heilman et al. . | |
| 4,218,555 | 8/1980 | Antonoplos et al. . | |
| 4,221,895 | 9/1980 | Woo . | |
| 4,225,497 | 9/1980 | Baudouin et al. . | |
| 4,225,498 | 9/1980 | Baudouin et al. . | |
| 4,231,934 | 11/1980 | Oba et al. . | |
| 4,234,712 | 11/1980 | Keller et al. . | |
| 4,237,262 | 12/1980 | Jones . | |
| 4,237,916 | 6/1981 | Jones . | |
| 4,239,883 | 12/1980 | Stenzenberger . | |
| 4,244,853 | 1/1981 | Serafini et al. . | |
| 4,250,096 | 2/1981 | Kvita et al. . | |
| 4,251,418 | 2/1981 | Chow et al. . | |
| 4,251,419 | 2/1981 | Heilman et al. . | |
| 4,251,420 | 2/1981 | Antonoplos et al. . | |
| 4,255,313 | 3/1981 | Antonoplos et al. . | |
| 4,266,047 | 5/1981 | Jablonski et al. . | |
| 4,269,961 | 5/1981 | Jones et al. . | |
| 4,271,079 | 6/1981 | Maeda et al. . | |
| 4,276,407 | 6/1981 | Bilow et al. . | |
| 4,288,583 | 9/1981 | Zahir et al. . | |
| 4,288,607 | 9/1981 | Bier et al. . | |
| 4,289,699 | 9/1981 | Oba et al. . | |
| 4,293,670 | 10/1981 | Robeson et al. . | |
| 4,297,472 | 10/1981 | Heiss . | |
| 4,297,474 | 10/1981 | Williams, III et al. . | |
| 4,298,720 | 11/1981 | Yamazaki et al. . | |
| 4,299,750 | 11/1981 | Antonoplos et al. . | |

4,299,946 11/1981 Balme et al. .
4,302,575 11/1981 Takekoshi .
4,323,662 4/1982 Oba et al. .
4,338,222 7/1982 Limburg et al. .
4,338,225 7/1982 Sheppard .
4,344,869 8/1982 Blinne et al. .
4,344,870 8/1982 Blinne et al. .
4,351,932 9/1982 Street et al. .
4,358,561 11/1982 Keske et al. .
4,360,644 11/1982 Naarmann et al. .
4,365,068 12/1982 Darms et al. .
4,375,427 3/1983 Miller et al. .
4,376,710 3/1983 Gardos et al. .
4,381,363 4/1983 Reinhart, Jr. .
4,389,504 6/1983 St. Clair et al. .
4,393,188 7/1983 Takahashi et al. .
4,395,497 7/1983 Naarmann et al. .
4,400,613 8/1983 Popelish .
4,405,770 9/1983 Schoenberg et al. .
4,407,739 10/1983 Naarmann et al. .
4,409,382 10/1983 Keller .
4,410,686 10/1983 Hefner, Jr. et al. .
4,414,269 11/1983 Lubowitz et al. .
4,417,039 11/1983 Reinhardt et al. .
4,417,044 11/1983 Parekh .
4,418,181 11/1983 Monacelli .
4,423,202 12/1983 Choe .
4,429,108 1/1984 Stephens .
4,438,273 3/1984 Landis .
4,438,280 3/1984 Monacelli .
4,446,191 5/1984 Miyadera et al. .
4,448,925 5/1984 Hanson .
4,460,783 7/1984 Nishikawa et al. .
4,465,809 8/1984 Smith .
4,467,011 8/1984 Brooks et al. .
4,476,184 10/1984 Lubowitz et al. .
4,476,295 10/1984 Stephens .
4,482,683 11/1984 Quella et al. .
4,485,140 11/1984 Gannett et al. .
4,485,231 11/1984 Landis .
4,489,027 12/1984 St. Clair et al. .
4,504,632 3/1985 Holub et al. .
4,507,466 3/1985 Tomalia et al. .
4,510,272 4/1985 Loszewski .
4,515,962 5/1985 Renner .
4,519,926 5/1985 Basalay et al. .
4,520,198 5/1985 D'Alelio et al. .
4,526,838 7/1985 Fujioka et al. .
4,533,692 8/1985 Wolfe et al. .
4,533,693 8/1985 Wolfe et al. .
4,533,724 8/1985 Wolfe et al. .
4,535,117 8/1985 Mathis et al. .
4,536,559 8/1985 Lubowitz et al. .
4,547,553 10/1985 Lubowitz et al. .
4,555,563 11/1985 Hefner, Jr. et al. .
4,556,697 12/1985 Curatolo et al. .
4,556,705 12/1985 McCready .
4,558,120 12/1985 Tomalia et al. .
4,562,231 12/1985 Dean .
4,562,232 12/1985 Smith .
4,563,498 1/1986 Lucas .
4,563,514 1/1986 Liu et al. .
4,564,553 1/1988 Pellegrini et al. .
4,567,216 1/1986 Qureshi et al. .
4,567,240 1/1986 Hergenrother et al. .
4,568,737 2/1986 Tomalia et al. .
4,574,144 3/1986 Yates, III et al. .
4,574,148 3/1986 Wicker, Jr. et al. .
4,574,154 3/1986 Okamoto et al. .
4,576,857 3/1986 Gannett et al. .
4,577,034 3/1986 Durvasula .
4,578,433 3/1986 Muenstedt et al. .
4,578,470 3/1986 Webb .
4,584,364 4/1986 Lubowitz et al. .
4,587,329 5/1986 Tomalia et al. .
4,590,363 5/1986 Bernard .
4,599,383 7/1986 Satoji .
4,600,769 7/1986 Kumar et al. .
4,604,437 8/1986 Renner .
4,608,414 8/1986 Kitsunai et al. .
4,608,426 8/1986 Stern .
4,609,683 9/1986 Grigsby, Jr. et al. ................ 528/64 X
4,611,022 9/1986 Hefner, Jr. .
4,611,048 9/1986 Peters .
4,614,767 9/1986 Dean .
4,615,832 10/1986 Kress et al. .
4,616,070 10/1986 Zeiner et al. .
4,616,071 10/1986 Holubka .
4,617,390 10/1986 Hoppe et al. .
4,624,888 11/1986 St. Clair et al. .
4,628,067 12/1986 Chen, Sr. et al. .
4,628,079 12/1986 Zecher et al. .
4,629,777 12/1986 Pfeifer .
4,631,337 12/1986 Tomalia et al. .
4,638,027 1/1987 Mark et al. .
4,640,944 2/1987 Brooks .
4,649,080 3/1987 Fischer et al. .
4,654,410 3/1987 Kashiwame et al. .
4,657,973 4/1987 Endo et al. .
4,657,977 4/1987 Peters .
4,657,987 4/1987 Rock et al. .
4,657,990 4/1987 Daoust et al. .
4,660,057 4/1987 Watanabe et al. .
4,661,604 4/1987 Lubowitz et al. .
4,663,378 5/1987 Allen .
4,663,399 5/1987 Peters .
4,663,423 5/1987 Yamada et al. .
4,663,424 5/1987 Stix et al. .
4,663,425 5/1987 Evers et al. .
4,680,326 7/1987 Leland et al. .
4,680,377 7/1987 Matsumura et al. .
4,684,714 8/1987 Lubowitz et al. .
4,686,242 8/1987 Turner et al. ........................ 528/64 X
4,690,972 9/1987 Johnson et al. .
4,691,025 9/1987 Domeier et al. .
4,694,064 9/1987 Tomalia et al. .
4,695,610 9/1987 Egli et al. .
4,699,975 10/1987 Katto et al. .
4,703,081 10/1987 Blackwell et al. .
4,708,983 11/1987 Liang .
4,709,004 11/1987 Dai .
4,709,006 11/1987 Tsai et al. .
4,709,008 11/1987 Shimp .
4,714,768 12/1987 Hemkielm et al. .
4,716,212 12/1987 Gaughan .
4,719,283 1/1988 Bartmann .
4,727,118 2/1988 Egami .
4,728,742 3/1988 Renner .
4,730,030 3/1988 Hahn et al. .
4,737,550 4/1988 Tomalia .
4,739,030 4/1988 Lubowitz et al. .
4,739,075 4/1988 Odagiri et al. .
4,739,115 4/1988 Byrd et al. .
4,740,563 4/1988 McCready et al. .
4,740,564 4/1988 McCready et al. .
4,740,584 4/1988 Shimp .
4,742,166 5/1988 Renner .
4,748,227 5/1988 Matzner et al. .
4,755,584 7/1988 Tomioka et al. .
4,755,585 7/1988 Hanson et al. .
4,757,118 7/1988 Das et al. .
4,757,128 7/1988 Domb et al. .
4,757,150 7/1988 Guggenheim et al. .
4,759,986 7/1988 Marikar et al. .

| | | |
|---|---|---|
| 4,760,106 | 7/1988 | Gardner et al. . |
| 4,764,427 | 8/1988 | Hara et al. . |
| 4,766,180 | 8/1988 | Wong . |
| 4,766,197 | 8/1988 | Clendinning et al. . |
| 4,769,424 | 9/1988 | Takekoshi et al. . |
| 4,769,426 | 9/1988 | Iwasaki et al. . |
| 4,769,436 | 9/1988 | Beck et al. . |
| 4,774,282 | 9/1988 | Qureshi . |
| 4,777,208 | 10/1988 | Hefner, Jr. . |
| 4,778,830 | 10/1988 | Streu et al. . |
| 4,778,859 | 10/1988 | Ai et al. . |
| 4,778,898 | 10/1988 | Vonlanthen et al. . |
| 4,786,669 | 11/1988 | Dewhirst . |
| 4,786,685 | 11/1988 | Takida et al. . |
| 4,786,713 | 11/1988 | Rule et al. . |
| 4,798,685 | 1/1989 | Yaniger . |
| 4,798,686 | 1/1989 | Hocker et al. . |
| 4,798,882 | 1/1989 | Petri . |
| 4,801,676 | 1/1989 | Hisgen et al. . |
| 4,801,677 | 1/1989 | Eckhardt et al. . |
| 4,804,722 | 2/1989 | Hesse et al. . |
| 4,804,724 | 2/1989 | Harris et al. . |
| 4,806,407 | 2/1989 | Skinner et al. . |
| 4,808,717 | 2/1989 | Saito et al. . |
| 4,812,518 | 3/1989 | Haubennestel et al. . |
| 4,812,534 | 3/1989 | Blakely . |
| 4,812,552 | 3/1989 | Cliffton et al. . |
| 4,812,588 | 3/1989 | Schrock . |
| 4,814,416 | 3/1989 | Poll . |
| 4,814,417 | 3/1989 | Sugimori . |
| 4,814,421 | 3/1989 | Rosenquist . |
| 4,814,472 | 3/1989 | Lau . |
| 4,816,503 | 3/1989 | Cunningham et al. . |
| 4,816,526 | 3/1989 | Bristowe et al. . |
| 4,816,527 | 3/1989 | Rock . |
| 4,816,556 | 3/1989 | Gay et al. . |
| 4,820,770 | 4/1989 | Schleifstein . |
| 4,826,927 | 5/1989 | Schmid et al. . |
| 4,826,997 | 5/1989 | Kirchhoff . |
| 4,827,000 | 5/1989 | Schwartz . |
| 4,829,138 | 5/1989 | Barthelemy . |
| 4,835,197 | 5/1989 | Mercer . |
| 4,837,256 | 6/1989 | Gardner et al. . |
| 4,839,378 | 6/1989 | Koyama et al. . |
| 4,845,150 | 7/1989 | Kovak et al. . |
| 4,845,167 | 7/1989 | Alston et al. . |
| 4,845,185 | 7/1989 | Teramoto et al. . |
| 4,845,278 | 7/1989 | Erhan . |
| 4,847,333 | 7/1989 | Lubowitz et al. . |
| 4,851,280 | 7/1989 | Gupta . |
| 4,851,287 | 7/1989 | Hartsing, Jr. . |
| 4,851,494 | 7/1989 | Eldin et al. . |
| 4,851,495 | 7/1989 | Sheppard et al. . |
| 4,851,496 | 7/1989 | Poll et al. . |
| 4,851,501 | 7/1989 | Lubowitz et al. . |
| 4,851,505 | 7/1989 | Hayes . |
| 4,861,855 | 8/1989 | Bockrath et al. . |
| 4,861,882 | 8/1989 | Hergenrother et al. . |
| 4,861,915 | 8/1989 | Clendinning et al. . |
| 4,861,924 | 8/1989 | Riggs . |
| 4,868,270 | 9/1989 | Lubowitz et al. . |
| 4,871,475 | 10/1989 | Lubowitz et al. . |
| 4,874,834 | 10/1989 | Higashi et al. . |
| 4,876,325 | 10/1989 | Olson et al. . |
| 4,876,328 | 10/1989 | Lubowitz et al. . |
| 4,876,330 | 10/1989 | Higashi et al. . |
| 4,891,167 | 1/1990 | Clendinning et al. . |
| 4,891,408 | 1/1990 | Newman-Evans . |
| 4,891,460 | 1/1990 | Ishii . |
| 4,895,892 | 1/1990 | Satake et al. . |
| 4,895,924 | 1/1990 | Satake et al. . |
| 4,897,527 | 1/1990 | Cripps et al. . |
| 4,902,335 | 2/1990 | Kume et al. . |
| 4,902,440 | 2/1990 | Takeyama et al. . |
| 4,902,769 | 2/1990 | Cassidy et al. . |
| 4,902,773 | 2/1990 | Bodnar et al. . |
| 4,916,210 | 4/1990 | Jackson . |
| 4,916,235 | 4/1990 | Tan et al. . |
| 4,919,992 | 4/1990 | Blundell et al. . |
| 4,923,752 | 5/1990 | Cornelia . |
| 4,927,899 | 5/1990 | Michaud et al. . |
| 4,927,900 | 5/1990 | Michaud et al. . |
| 4,931,531 | 6/1990 | Tamai et al. . |
| 4,931,540 | 6/1990 | Mueller et al. . |
| 4,935,523 | 6/1990 | Lubowitz et al. . |
| 4,958,031 | 9/1990 | Sheppard et al. . |
| 4,965,336 | 10/1990 | Lubowitz et al. . |
| 4,973,662 | 11/1990 | Odagiri et al. . |
| 4,980,481 | 12/1990 | Lubowitz et al. . |
| 4,981,922 | 1/1991 | Sheppard et al. . |
| 4,985,568 | 1/1991 | Lubowitz et al. . |
| 4,990,624 | 2/1991 | Sheppard et al. . |
| 4,996,101 | 2/1991 | Landis et al. . |
| 5,003,035 | 3/1991 | Tsai et al. . |
| 5,011,905 | 4/1991 | Lubowitz et al. . |
| 5,066,541 | 11/1991 | Lubowitz et al. . |
| 5,066,776 | 11/1991 | Russeler et al. . |
| 5,071,941 | 12/1991 | Lubowitz et al. . |
| 5,075,537 | 12/1991 | Lorenzen et al. . |
| 5,082,905 | 1/1992 | Lubowitz et al. . |
| 5,086,154 | 2/1992 | Camberlin et al. . |
| 5,087,701 | 2/1992 | Lubowitz et al. . |
| 5,104,967 | 4/1992 | Sheppard et al. . |
| 5,109,105 | 4/1992 | Lubowitz et al. . |
| 5,111,026 | 5/1992 | Ma . |
| 5,112,936 | 5/1992 | Okamoto . |
| 5,112,939 | 5/1992 | Lubowitz et al. . |
| 5,115,087 | 5/1992 | Sheppard et al. . |
| 5,116,935 | 5/1992 | Lubowitz et al. . |
| 5,120,819 | 6/1992 | Lubowitz et al. . |
| 5,126,410 | 6/1992 | Lubowitz et al. . |
| 5,144,000 | 9/1992 | Sheppard et al. . |
| 5,151,487 | 9/1992 | Lubowitz et al. . |
| 5,155,206 | 10/1992 | Lubowitz et al. . |
| 5,159,055 | 10/1992 | Sheppard et al. . |
| 5,175,233 | 12/1992 | Lubowitz et al. . |
| 5,175,234 | 12/1992 | Lubowitz et al. . |
| 5,175,304 | 12/1992 | Sheppard . |
| 5,198,526 | 3/1993 | Lubowitz et al. . |
| 5,210,213 | 5/1993 | Sheppard et al. . |
| 5,216,117 | 6/1993 | Sheppard et al. . |
| 5,227,461 | 7/1993 | Lubowitz et al. . |
| 5,230,956 | 7/1993 | Cole et al. . |
| 5,239,046 | 8/1993 | Lubowitz et al. . |
| 5,254,605 | 10/1993 | Kim et al. . |
| 5,268,519 | 12/1993 | Sheppard et al. . |
| 5,286,811 | 2/1994 | Lubowitz et al. . |
| 5,338,532 | 8/1994 | Tomalia et al. . |
| 5,344,894 | 9/1994 | Lubowitz . |

FOREIGN PATENT DOCUMENTS

| | | |
|---|---|---|
| 0309649 | 4/1989 | European Pat. Off. . |
| 0310735 | 4/1989 | European Pat. Off. . |
| 0311735 | 4/1989 | European Pat. Off. . |
| 0317754 | 5/1989 | European Pat. Off. . |
| 0323540 | 7/1989 | European Pat. Off. . |
| 0336856 | 10/1989 | European Pat. Off. . |
| 0405128 | 1/1991 | European Pat. Off. . |
| 0418406 | 3/1991 | European Pat. Off. . |
| 0334778 | 4/1992 | European Pat. Off. . |
| 71.00975 | 1/1971 | France . |
| 2166209 | 8/1973 | France . |
| 2210635 | 7/1974 | France . |
| 2272119 | 12/1975 | France . |

| | | |
|---|---|---|
| 2303818 | 10/1976 | France . |
| 1951632 | 5/1971 | Germany . |
| 57100111 | of 0000 | Japan . |
| 1453625 | 12/1973 | Japan . |
| 58059219 | 10/1981 | Japan . |
| 1210408A | 2/1988 | Japan . |
| 907105 | 10/1962 | United Kingdom . |
| 1069061 | 5/1967 | United Kingdom . |
| 1099096 | 1/1968 | United Kingdom . |
| 1453625 | 10/1976 | United Kingdom . |
| 2002387 | 2/1977 | United Kingdom . |
| 2002378 | 3/1982 | United Kingdom . |
| 81/01855 | 7/1981 | WIPO . |
| 84/04313 | 11/1984 | WIPO . |

OTHER PUBLICATIONS

Walton, A New Conjugated Network Polymer as an Electrical Conductor and Thermally Stable Plastic, Am. Chem., Soc. Org. Coat Plast. Chem., vol. 42, 595–599 1980.

Serafini et al., Thermally Stable Polyimides from Solutions of Monomeric Reactants, Journal of Applied Polymer Science, vol. 16 pp. 905–915 1972.

Spillman et al., Coploymers of Poly(Para–Phenylene Terephthalamide) Containing a Thermally Activated Cross–Linking Agent, PMSE vol. 68, Spring Meetings 139–140 1993.

Radlmann, et al., New Synthesis of Poly(ether Ketones). (44195h), Chem Abstracts vol. 72, 1970, p. 44187 1970.

Bryant, et al., Synthesis and Properties of Phenylethnyl–Terminated Polyimides, Polymer PrePrints, vol. 34, No. 1, 566–567 Mar. 1993.

Crivello et al., Polyimidothioether–Polysulfide Block Polymers, Polymer Sci., Polymer Chem. Ed., vol. 13, pp. 1819–1842 1975.

Frazer, High Temperature Resistant Polymers, Interscience Publishers, John Wiley & Sons, Inc., 139–213 1968.

St. Clair et al., The Development of Aerospace Polyimide Adhesives, Mittal (ed), Polyimides–Synthesis Characterization and Applications, Plenum Press, NY, vol. 2, pp. 977–1041 1973.

Serafini, et al., A Review of Processable High Temperature Resistant Addition–type Laminating Resins, Mittal (ed), Polyimides–Synthesis, Characterization and Applications, Plenum Press, NY, vol. 1, PP. 89–95 1973.

Stenson, Polycyanurates Find Applications; Their Chemistry Remains Puzzling, Science/Technology, 208 ACS National Meeting, Washington, D.C., C&EN Northeast News Bureau 30–31 Sep. 1994.

Stoakley, et al., Low–Dielectric–Constant Polyimide/Glass Composites, NASA Tech. Briefs p. 24 Apr. 1994.

Bartolotta, Predicting Fatigue Lives of Metal–Matrix/Fiber Composites, Nasa Tech Briefs pp. 28,30 Apr. 1994.

Vannucci, et al., Improved PMR Polyimides for Heat–Stable Laminates, NASA Tech Briefs pp. 30–31 Apr. 1994.

Bryant, et al., Phenylethynyl End–Capping Reagents and Reactive Diluents, NASA Tech Briefs pp. 36–37 Apr. 1994.

Jensen, et al., Phenylethynyl–Terminated Ploy(Arylene Ethers), NASA Tech Briefs p. 37 Apr. 1994.

Buckley, et al., Processable Polyimides for High Temperature Applications, 36th International SAMPE Symposium pp. 1172–1181 Apr. 1991.

Edwards, et al. Constituents of the Higher Fungi. Part XIII.[1] 2–Arly–3–methoxymaleic Anhydrides from Pulvinic Acid Derivatives. A Convenient Method for Determination of Structure of Fungaland Lichen Pulvinic Acid Derivatives, Journal of The Chemical Society pp.1538–1542 1973.

Kwiatkowski, et al., Thermosetting Diphenyl Sulfone–Based Malcimides, Journal of Polymer Science, vol. 13, pp. 961–972 1975.

Lyle, et al., Polyarylene Ethers: Maleimides, Nadimides and Blends, The Interdisciplinary Symposium on Recent Advances in Polymides and Other High Performance Polymers, San Diego, California pp. K–1–K–7, Jan. 1990.

Roberts, et al., Effect of Solution Concentration and Aging Conditions on PMR–15 Resin, SAMPE Journal, pp. 24–28, 213, Mar/Apr. 1986.

Southcott, et al., "The Development of Processable, Fully Imidized, Polyimides for High–Temperature Applications", High Perform. Polym. 6, pp. 1–12, Printed in UK, 1994.

METHODS FOR MAKING LIQUID MOLDING COMPOUNDS USING DIAMINES AND DICYANATES

REFERENCE TO RELATED APPLICATION

The present application is a divisional application based upon U.S. patent application Ser. No. 07/168,289 filed Mar. 15, 1988. The present application also claims the benefit of U.S. patent application Ser. No. 08/327,942, filed Oct. 21, 1994.

TECHNICAL FIELD

The present invention relates to a family of relatively low-viscosity monomers that can be used in injection molding to fabricate high performance, advanced composites without the use of solvents. The composite parts are generally thermoset compositions with stable melts at moderate temperatures. Diamine diluents can be added to the monomers to prepare block copolymers upon curing.

BACKGROUND OF THE INVENTION

Recently, chemists have sought to synthesize oligomers for high performance advanced composites suitable for aerospace applications. These composites should exhibit solvent resistance; be tough, impact resistant, and strong; be easy to process; and be thermoplastic. Oligomers and composites that have thermo-oxidative stability and, accordingly, can be used at elevated temperatures are particularly desirable.

While epoxy-based composites are suitable for many applications, their brittle nature and susceptibility to thermal or hydrolytic degradation make them inadequate for many aerospace applications, especially those applications which require thermally stable, tough composites. Accordingly, research has recently focused on polyimide composites to achieve an acceptable balance between thermal stability, solvent resistance, and toughness. Still the maximum temperatures for use of the polyimide composites, such as PMR-15, are about 600°–625° F., since they have glass transition temperatures of about 690° F. PMR-15 still suffers, however, from brittleness.

There has been a progression of polyimide sulfone compounds synthesized to provide unique properties or combinations of properties. For example, Kwiatkowski and Brode synthesized maleic-capped linear polyarylimides as disclosed in U.S. Pat. No. 3,839,287. Holub and Evans synthesized maleic- or nadic-capped, imido-substituted polyester compositions as disclosed in U.S. Pat. No. 3,729,446. We synthesized thermally stable polysulfone oligomers as disclosed in U.S. Pat. No. 4,476,184 or U.S. Pat. No. 4,536,559, and have continued to make advances with polyetherimidesulfones, polybenzoxazolesulfones, polybutadienesulfones, and "star" or "star-burst" multidimensional oligomers. We have shown surprisingly high glass transition temperatures yet reasonable processing and desirable physical properties in many of these oligomers and their composites.

Polybenzoxazoles and other heterocycle oligomers, such as those disclosed in U.S. Pat. Nos. 4,965,336 and 4,868,270, may be used at temperatures up to about 750°–775° F., since these composites have glass transition temperatures of about 840° F. Some aerospace applications need composites which have even higher use temperatures while maintaining toughness, solvent resistance, ease of processing, formability, strength, and impact resistance.

Multidimensional oligomers, such as disclosed in our U.S. patent application Ser. No. 06/810,817 (now abandoned) and in U.S. Pat. No. 5,210,213, are easier to process than some advanced composite oligomers since they can be handled at lower temperatures. Upon curing, however, the oligomers crosslink (homopolymerize) through their end caps so that the thermal resistance of the resulting composite is markedly increased with only a minor loss of stiffness, matrix stress transfer (impact resistance), toughness, elasticity, and other mechanical properties. Glass transition temperatures above 950° F. are achievable.

Commercial polyesters, when combined with well-known diluents, such as styrene, do not exhibit satisfactory thermal and oxidative resistance to be useful for aircraft or aerospace applications. Polyarylesters are often unsatisfactory, also, since the resins often are semicrystalline which may makes them insoluble in laminating solvents, intractable in fusion, and subject to shrinking or warping during composite fabrication. Those polyarylesters that are soluble in conventional laminating solvents remain so in composite form, thereby limiting their usefulness in structural composites. The high concentration of ester groups contributes to resin strength and tenacity, but also makes the resin susceptible to the damaging effects of water absorption. High moisture absorption by commercial polyesters can lead to distortion of the composite when it is loaded at elevated temperature.

High performance, aerospace, polyester advanced composites, however, can be prepared using crosslinkable, end capped polyester imide ether sulfone oligomers that have an acceptable combination of solvent resistance, toughness, impact resistance, strength, processibility, formability, and thermal resistance. By including Schiff base (—CH=N—), imidazole, thiazole, or oxazole linkages in the oligomer chain, the linear, advanced composites formed with polyester oligomers of our U.S. patent application Ser. No. 06/726,259 (now abandoned) can have semiconductive or conductive properties when appropriately doped.

Conductive and semiconductive plastics have been extensively studied (see, e.g., U.S. Pat. Nos. 4,375,427; 4,338,222; 3,966,987; 4,344,869; and 4,344,870), but these polymers do not possess the blend of properties which are essential for aerospace applications. That is, the conductive polymers do not possess the blend of (1) toughness, (2) stiffness, (3) elasticity, (4) ease of processing, (5) impact resistance (and other matrix stress transfer capabilities), (6) retention of properties over a broad range of temperatures, and (7) high temperature resistance that is desirable on aerospace advanced composites. The prior art composites are often too brittle.

Thermally stable multidimensional oligomers having semiconductive or conductive properties when doped with suitable dopants are also known and are described in our copending applications (including U.S. patent application Ser. No. 06/773,381 to Lubowitz, Sheppard and Torre). The linear arms of the oligomers contain conductive linkages, such as Schiff base (—N=CH—) linkages, between aromatic groups. Sulfone and ether linkages are interspersed in the arms. Each arm is terminated with a mono- or difunctional end cap (i.e. an end cap having one or two crosslinking functionalities) to allow controlled crosslinking upon heat-induced or chemically-induced curing. Other "semiconductive" oligomers are described in our other copending applications.

Polyamide oligomers and blends are described in our U.S. Pat. Nos. 4,935,523 and 4,847,333, and polyetherimide oligomers and blends are described in our U.S. Pat. No. 4,851,495.

Polyamideimides are generally injection-moldable, amorphous, engineering thermoplastics which absorb water (swell) when subjected to humid environments or immersed in water. Polyamideimides are generally described in the following patents: U.S. Pat. No. 3,658,938; U.S. Pat. Nos. 4,628,079; 4,599,383; 4,574,144; or 3,988,344. The thermal integrity and solvent-resistance can be greatly enhanced by capping amideimide backbones with monomers that present one or two crosslinking functionalities at each end of the oligomer, as described in U.S. patent application Ser. No. 07/092,740 (now abandoned); which resulted in U.S. Pat. No. 5,104,967, but the injection molding capability probably is lost.

The high performance resins that we described in our earlier applications and summarized here can be processed into prepregs, but require that solvents be used for this processing. The management of the solvent during the manufacturing process accordingly, presents problems, such as ease of handling, convenience, cost, waste management, and personal safety. These problems are alleviated in a process that can eliminate the solvents.

While prepreg layup and curing is cost effective for manufacturing one class of aerospace parts, an injection molding compound in liquid form would allow the manufacture of large parts (including complex curvature) quickly and with comparatively low investment. Composite molds may be used when the molding compounds cure at relatively low pressures. Reinforced parts can be made in the molds by including filaments or fabrics in the mold. Injection molding eliminates the high labor cost of prepreg layup that is incurred for complex shapes, especially those requiring precise shapes to within a close tolerance. Often milling is required to make such shapes, with the resultant equipment (capital) and labor costs.

Several resins for reaction injection molding (RIM) or resin transfer molding (RTM) have been developed, including urethanes, esters, ureas, acrylesterols, triazathanes, and cyclopentadienes (i.e., PDCPD, such as METTON polymers available from Hercules, Inc.). These molding resins, however, often exhibit premature gelling, a problem that is overcome with the family of liquid molding compounds of the present invention.

SUMMARY OF THE INVENTION

Liquid molding compounds of the present invention are suitable for reaction injection molding (RIM) or resin transfer molding (RTM) to form thermoset composites with or without fiber reinforcement. The compounds are free of solvents and can be quickly cured at modest temperatures and pressures to produce rigid composites that offer a wide range of flexibility and resilience. The liquid molding compounds are characterized by including crosslinking (i.e. unsaturated hydrocarbon) groups at the ends of the polymer backbone. The crosslinking groups generally are radicals selected from the group consisting of:

$D_i$—Ø— wherein i=1 or 2 (i.e. mono- or difunctional);

Ø=phenyl;

D=

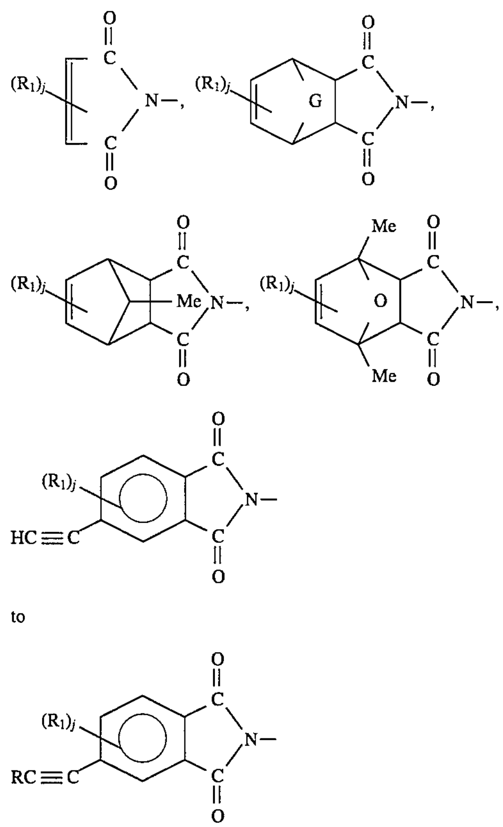

to

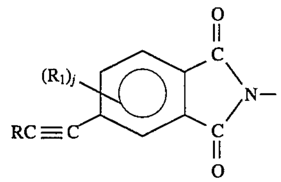

$R_1$=lower alkyl, lower alkoxy, aryl, aryloxy, substituted alkyl, substituted aryl (the substituents including hydroxyl or halo groups), halogen, or mixtures thereof;

j=0, 1 or 2;

G=—$CH_2$—, —O—, —S—, —$SO_2$—, —SO—, —CO—, —CHR—, or —$C(R)_2$—;

T=methallyl or allyl;

Me=methyl; and

R=hydrogen, lower alkyl, or phenyl and, preferably, wherein D=

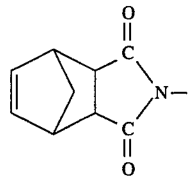

The phenyl group may be replaced with a pyrimidine group, but these compounds are not preferred.

The compounds are generally polyethers made from polyether diols or triols, such as polypropylene glycol triol of the general formula:

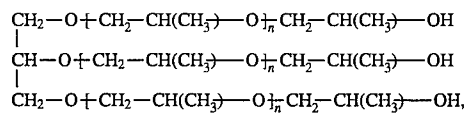

condensed with an acid halide cap of the formula: $D_i$—Ø—COX or a nitro cap of the formula D-Ø-$NO_2$. Other suitable reactants, include esters, urethanes, amides, imides, ureas, and mixtures (or blends) thereof, especially those reactants, such as oxypropylene triamine, that have aliphatic backbones comparable to the triol described above. The cap may include a hydroxyl, an amine, an acid halide, or a nitro functionality as necessary to complete the reaction. Anhydrides containing the unsaturation of the D radical may also be used, especially with oxypropylene triamine.

BEST MODE CONTEMPLATED FOR MAKING AND USING THE INVENTION

The present invention of liquid molding resins describes a family of relatively low-viscosity oligomers that are suitable for reaction injection molding (RIM) or resin transfer molding (RTM) at modest temperatures and pressures to form high performance, thermoset composites without the use of the solvents that are customarily required to make comparable composites from prepregs. The composites are generally rigid but they offer a wide range of flexibility and resilience.

The liquid molding compounds include mono- or difunctional, crosslinking groups (i.e., groups having one or two crosslinking sites) of the same nature as our earlier high performance resins. These groups improve the solvent resistance and thermo-oxidative stability of the composites. The compounds also include polymeric backbones of ethers, esters, urethanes, amides, imides, ureas, or mixtures (i.e. blends) of two or more of these compounds. The liquid molding compounds are prepared by reacting the crosslinking end-cap monomers with polyether diols or triols, esters, or the like, or in simultaneous condensation reactions that include the precursors of such backbones and suitable end-cap monomers.

The crosslinking end cap monomers have hydrocarbon unsaturation and generally include a radical selected from the group consisting of:

$D_i$—Ø— wherein $i$=1 or 2;

Ø=phenyl;

D=

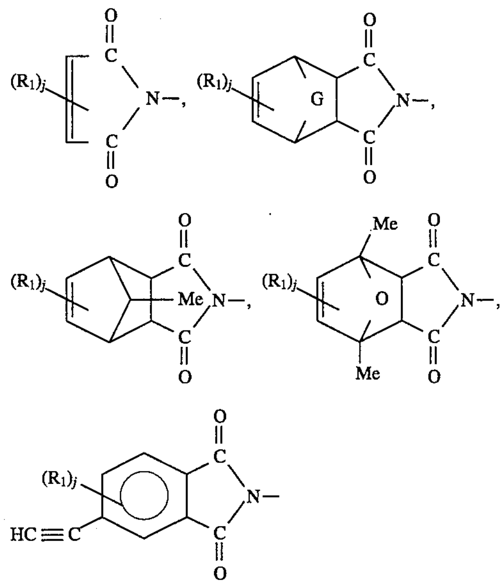

to

-continued

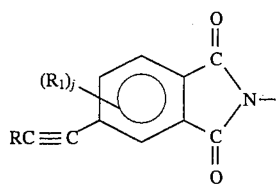

$R_1$=lower alkyl, lower alkoxy, aryl aryloxy, substituted alkyl, substituted aryl (the substituents including hydrozyl or halo groups), halogen, or mixtures thereof;

G=—$SO_2$—, —S—, —O—, —$CH_2$—, —CO—, —SO—, —CH(R)—, or —$C(R)_2$—;

$i$=1 or 2;

$j$=0, 1 or 2;

T=methallyl or allyl;

Me=methyl; and

R=hydrogen, lower alkyl, or phenyl.

A particularly preferred end-cap is:

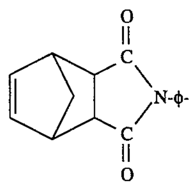

because of its relatively low cost and its relatively low activation (i.e. curing) temperature. The resulting thermoset composites have relatively high thermal stability.

Suitable ether precursors are characterized by the aliphatic triol, polypropylene glycol triol of the general formula:

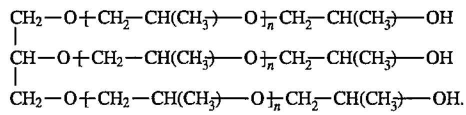

diols or triols of this general type can be reacted with $D_i$—Ø—COX to form capped ethers through the —OH/—COX ester condensation. Compounds of the formula: $D_i$—Ø—COX are readily prepared from the corresponding anhydrides by condensation with amino- or diamino benzoic acid, as explained in U.S. Pat. No. 4,604,437. Alternatively, the ether precursors can be condensed with a nitro end cap monomer formed by reacting the anhydrides with nitroaniline to form an ether linkage between the precursor and the cap.

Although not preferred because of cost and complexity, the acid halide end-cap monomer can be made by condensing the anhydrides with a pyrimidine of the formula:

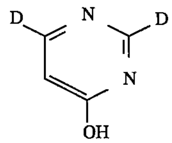

The precursor amines are describes in U.S. Pat. No. 3,461,461. The resulting intermediate can be reacted with nitrobenzoic acid halide or halobenzoic acid halide to form an acid halide end-cap monomer of the formula:

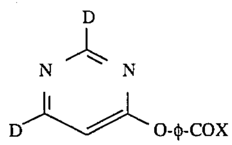

Polyamines, such as polyoxypropylene triamine (a counterpart of the propylene glycol triol) can be reacted directly with the anhydrides to form imide caps. Alternately, the terminal amino groups can be condensed with —COX of the end cap monomer to form an amide linkage. The absence of a phenyl radical adjacent the hydrogen unsaturation in the polyamine/anhydride condensation may impact the performance and physical properties of the resulting composites.

Moldable ureas can also be prepared by reacting the anhydride used to form the $D_i$—Ø— groups with an aliphatic, or aromatic, or aliphatic and aromatic diamine, such as phenylenediamine, with:

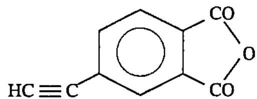

and a compound of the formula:

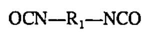

to form a capped reactive polyurea of the general formula:

$$(D)_i R_2\text{—NHCONH—}R_1\text{—NHCONH—}R_2(D)_i$$

wherein $i=1$ or 2;

$R_2$=an aliphatic or aromatic residue of the diamine; (i.e., —Ø— if phenylene diamine is used) and $R_1$=an aliphatic or aromatic residue.

The OCN—$R_1$—NCO compounds are described in U.S. Pat. No. 4,599,383, and generally include aliphatic segments. Generally an aliphatic diamine would also be used.

Polyoxypropylene triamine can be reacted with OCN—$R_1$—NCO, a diamine, and a suitable end cap to form a liquid molding compound. In this case, $R_1$ is generally a lower alkyl of less than about five carbon atoms, and the diamine is a lower alkyl diamine.

Preferably, any of the liquid molding compounds has an average formula weight below about 5000, and, generally, as low as about 1000.

The liquid molding compounds of the present invention can be improved by blending them with reactive diluents. Suitable diluents are aliphatic diamines, including, for example, 1,8-diaminooctane; 1,7-diaminoheptane; 1-5-diaminopentane; or 1,3-diaminopropane (i.e., diaminoalkyls). During curing, diamines of this type can react with the liquid molding compounds to form block copolymers.

The corresponding anhydrides used for direct reaction with the polyamines or for preparation of the nitro, acid halide, or phenol end cap monomers, of course, are selected from the group consisting of:

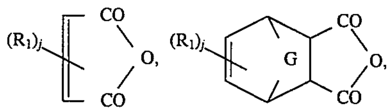

-continued

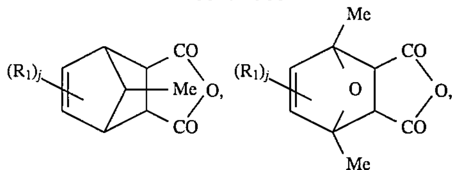

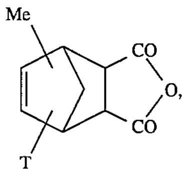

or

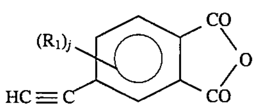

wherein $R_1$, G, Me, T, and j are as previously defined. In the direct condensation of the polyamines and anhydrides, only one crosslinking site is available at each chain terminus.

The polyols, such as polypropylene glycol triol, can have their chains extended by the nitro/phenol condensation using dinitro compounds. The end cap monomer in this case usually will be an imidophenol. Suitable dinitro compounds can be prepared, for example, by reacting MCTC (i.e., 5-(2,5-diketotetrahydrofuryl)-3-methyl-cyclohexene-1,2-dicarboxylic anhydride) with nitroaniline. Of course, other aliphatic dinitro compounds can be used, or an aromatic segment (particularly if it is short) may be incorporated into the liquid molding compound. Further chain extension can be achieved by adding dialcohols to the condensation mixture. Such chain extension, however, is likely to lead to the formation of undesirable, high-average-formula-weight oligomers. Therefore, usually the polyol will be condensed directly with the acid halide or nitro end cap monomer to form the product.

To limit the average formula weight of the products, the polyamines are generally condensed directly with the end cap anhydrides. Chain extension, however, can occur by using aliphatic dianhydrides, such as MCTC, and an imidophenylamine end cap monomer; by further extension with a dianhydride, a diamine, and a suitable end cap monomer; by using a dicarboxylic acid halide and an imidophenylamine end cap monomer, or in other ways known to those of ordinary skill in the art based upon this description.

It may be, possible to make liquid molding compounds simply by reacting the OCN—$R_1$—NCO compounds directly with imidophenylamine end cap monomers.

The liquid molding compounds of the present invention may be blends of the crosslinking oligomers and corresponding, compatible, noncrosslinking polymers. For example, the polyols can be condensed with a nitro end cap monomer and nitrobenzene to form a mixture of capped and uncapped molecules that still might provide the desired molding properties. It probably would be better, however, to blend the oligomer with a quenched polyol rather than to conduct the syntheses simultaneously.

The liquid molding compounds or blends can be mixed with reinforcing additives prior to or during injection to produce reinforced composites. The additives can be in continuous (fiber) or discontinuous (chopped or whisker) form and may be ceramic, organic, carbon (graphite), or glass as desired for the particular application.

Blends can improve the impact resistance of the cured composites without deleterious loss of solvent resistance (gained through the crosslinking caps). A 50—50 molar blend of the oligomer and polymer is probably the most desirable blend, but the ratio can be adjusted to provide the desired physical properties in the composite.

It is probably nonessential that the oligomer and polymer have identical repeating units. They need only be compatible when mixed. The polyethers might be mixed with polyesters, polyamides, or other polymers without loss of the molding properties.

While preferred embodiments have been described, those skilled in the art will recognize modifications or variations which might be made without departing from the inventive concept. Therefore, the description and claims should be interpreted liberally to cover the disclosed embodiments and their full range of equivalents with only such that limitation which is necessary in view of the pertinent prior art.

We claim:

1. A method for making a liquid molding compound of the formula

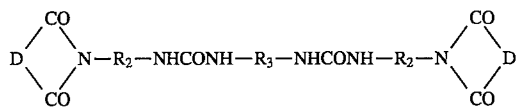

comprising the step of simultaneously condensing an unsaturated anhydride selected from the group consisting of:

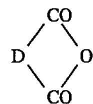

wherein

D=a hydrocarbon radical including an unsaturated functionality selected from the group consisting of:

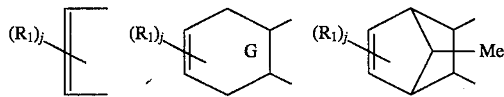

-continued

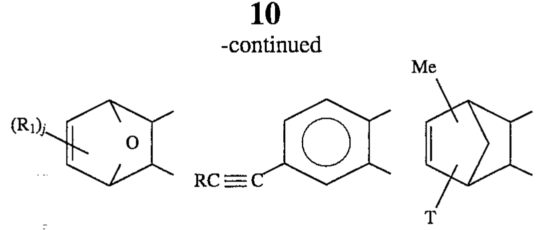

$R_1$=lower alkyl, aryl, substituted alkyl, substituted aryl, lower alkoxy, aryloxy, halogen, or mixtures thereof;

G=—$CH_2$—, —O—, —S—, —$SO_2$—, —SO—, —CO—, —CH(R)—, or —$C(R)_2$—;

j=0, 1, or 2;

T=allyl or methallyl;

Me=methyl; and

R=hydrogen, lower alkyl, or phenyl, with a diamine of the formula $H_2N$—$R_2$—$NH_2$ and a compound of the formula OCN—$R_3$—NCO, wherein $R_3$ is a hydrocarbon radical and $R_2$ is a hydrocarbon radical.

2. The method of claim 1 further comprising the step of blending the condensation product with an effective amount of a diluent.

3. The method of claim 2 wherein the diluent is an aliphatic diamine.

4. The method of claim 3 wherein the diluent is selected from the group consisting of:

1,8-diaminooctane;

1,7-diaminoheptane;

1,5-diaminopentane; and 1,3-diaminopropane.

5. The method of claim 1 wherein the diamine is aliphatic.

6. The method of claim 1 wherein the diamine is aromatic.

7. The method of claim 1 wherein $R_3$ is aliphatic.

8. The method of claim 7 wherein the diamine is aliphatic.

9. The method of claim 1 wherein the simultaneous condensation further includes polyoxypropylene triamine.

10. The method of claim 1 wherein D is either

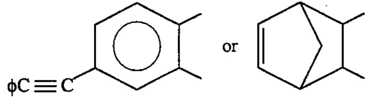

wherein φ=phenylene.

* * * * *